United States Patent [19]

Kennedy

[11] Patent Number: 4,852,573
[45] Date of Patent: Aug. 1, 1989

[54] IMPLANTABLE NEURAL ELECTRODE

[76] Inventor: Philip R. Kennedy, 3240 Indian Valley Trail, Atlanta, Ga. 30341

[21] Appl. No.: 128,721

[22] Filed: Dec. 4, 1987

[51] Int. Cl.$^4$ .......................... A61B 5/04; A61N 1/05
[52] U.S. Cl. .................................... 128/642; 128/784
[58] Field of Search ................ 128/642, 784, 785, 786

[56] References Cited

U.S. PATENT DOCUMENTS

| | | | |
|---|---|---|---|
| 3,089,483 | 5/1963 | Sheatz | 128/642 |
| 3,157,181 | 11/1964 | McCarty | 128/784 |
| 3,618,601 | 11/1971 | Richardson | 604/20 |
| 3,955,560 | 5/1976 | Stein et al. | |
| 4,046,141 | 9/1977 | DeLuca | 128/642 |
| 4,245,645 | 1/1981 | Arseneault et al. | 128/642 |
| 4,281,668 | 8/1981 | Richter et al. | |
| 4,623,355 | 11/1986 | Sawruk | |
| 4,649,936 | 3/1987 | Unger et al. | 128/784 |
| 4,662,884 | 5/1987 | Stensaas | |
| 4,750,499 | 6/1988 | Hoffen | 128/784 |

OTHER PUBLICATIONS

Legendy, C. R., et al., "A Multiple Floating Microelectrode for Chronic Implantation and Long-term Single Unit Recording in the Cat", *Electroencephalography and Clinical Neurophysiology*, '84, 58:285–288.

Jeutter, D. C. and Fromm, E., "A Modular Expandable Implantable Temperature Biotelemeter", *IEEE Transactions on Biomedical Engineering*, vol. VME-27, No. 5, May 1980.

Burne, B. D., et al., "Recording for Several Days from Single Cortical Neurons in Completely Unrestrained Cats," *Electroencephalography and Clinical Neurophysiology*, 1974, 36: 314–318.

*Primary Examiner*—Lee S. Cohen
*Attorney, Agent, or Firm*—Jones, Askew & Lunsford

[57] ABSTRACT

An electrode implantable in the brain or other area of neural activity to provide long term recording of electrical signals. The electrode comprises (a) a conducting wire, being insulated along its length except for a predetermined area, for conducting an electrical signal to or from the body from or to an extracorporeal transmitter or receiver; and (b) an open hollow insulating structure surrounding at least a portion of an exposed portion of the conducting wire for electrically isolating signal within the structure from that outside the structure. A method is disclosed for implanting the electrode. Also disclosed is the use of a viable nerve segment dissected from a remote part of the body, such as the sciatic nerve, to serve as an anchor for neurite growth from the brain into the insulator and in proximity to or contacting the exposed end of the wire.

21 Claims, 4 Drawing Sheets

IMPLANTABLE NEURAL ELECTRODE

FIELD OF THE INVENTION

The present invention relates to an apparatus for long term recording of signals produced by the body. More particularly, the present invention provides an implantable neural electrode for receiving electrical signals from the body or transmitting signals to the body. Also provided is a method for implanting the electrode.

BACKGROUND OF THE INVENTION

For a better understanding of this invention, several terms should be defined. The term "electrode" means a conductive device which is capable of transmitting an electrical signal. The term "nerve" describes a structure of fibers arranged in bundles held together by a connective tissue sheath. Stimuli are transmitted from the central nervous system to the periphery or the reverse through the fibers. The term "neural" means any structure that is composed of nerve cells or their components, or that on further development will give rise to nerve cells. The term "neurite" describes the filamentous neural projections that grow from nerves, usually from the nerve axon which normally conduct nerve impulses away from the cell body and the dendrites. The term "sciatic nerve" refers to the long nerve of the leg that extends from the back to the tip of the toes and carries both motor and sensory fiber. The term "cortex" describes the outer portion of an organ such as the brain as distinguished from the inner, or medullary, portion. The cerebral cortex is the layer of grey matter (1–4 mm thick) covering the entire outer surface of the cerebral hemisphere of mammals.

Muscle paralysis affects almost 100,000 quadriplegics in the United States and approximately 1 million persons worldwide. The optimum goal of the quadriplegic's rehabilitation is return of movement by activation of paralyzed muscles under direct control of the central nervous system. This has been achieved to some extent by functional neuromuscular stimulation. Using shoulder movements as control signals, the muscles of the paralyzed hand can be electrically stimulated to grasp and release. The problem remains to obtain better control signals because (1) shoulder control signals are insufficiently precise for the force and velocity control required by delicate movements, and (2) restoration of walking and complex forearm/hand movements and following spinal cord injury require multiple control signals. Precise, multiple control signals are found only within the central nervous system. Thus, to obtain information on the signals required for central nervous system control of reactivated muscles, there is a need to record a reliable usable signal over long periods such as months or years.

An even greater need in terms of numbers exists for a motor control device which would be beneficial for persons other than those with spinal cord injuries. Recording from cortical areas (other than area 4 of the cortex, as defined by current cortical mapping methods) such as the supplementary motor areas ("SMA") and premotor areas ("PMA") would be possible in patients who have a hemiparesis due to a stroke affecting the cortex supplied by the middle cerebral artery. In these lesions, the hemiparesis can be due to infarction of area 4 motor cortex and post-central cortex, but more rostral areas containing SMA and PMA are normally spared because they are supplied by the anterior cerebral artery. Recording from these areas in a stabilized stroke patient may be feasible because of the phenomenon of conditioning.

Conditioning of neuronal firing patterns has been demonstrated in performing monkeys, where monkeys were rewarded for activating neurons at particular firing rates, or activating particular neurons. The monkeys even succeeded in activating one neuron and suppressing the activity of another, the activity of both neurons being recorded simultaneously through the same electrode. This not only suggests that the desired neurons can be conditioned to fire at specific rates, but that undesirable neurons can be suppressed if contribution to unwanted background activity, thus physiologically improving the signal-to-noise ratio.

Conditioning of neuronal activity is even more likely to be successful in the strongly motivated human. Scientists have shown that the supplementary motor area of humans is under voluntary control. Subjects were asked to think about moving a finger but not actually move it. Cerebral blood flow (an indicator of neuronal activity) increased in the SMA but not in area 4. These studies in the human, plus the studies at the single cell level in sub-human primates, imply a high probability that humans can condition the activity of individual neurons.

There is yet another significant feature about recording multiple neurons: a wealth of basic neurophysiological data could become available. Questions regarding the functional organization of adjacent neurons, their relative activities during sensory perception, and their relative coordinated activities during motor output could be determined. Relative activity during conditioning and during learning of new tasks could be studied. Furthermore, implanting electrodes over different cortical areas, for example, area 4 and the SMA, could demonstrate functional interactions in a manner unavailable by any other means.

Efforts to implant electrodes have met with some success, but still encounter many problems. Typically, a wire or wires is implanted in the cortex, the wire is immobilized on the skull in some manner and connected to an amplification and recording device. These methods and devices are deficient in that movement of the electrode within the skull can disrupt signal transmission or cause signal artifacts. Nonflexibility of the electrode can cause, in addition to signal disruption, damage to the cortex. Moreover, there is the possibility of local tissue reaction to the presence of a foreign body or scar tissue formation over time which can decrease the usefulness of the electrode and the signal transmitted. Infection due to electrode wires can cause deleterious effects. Current implant electrodes have been used to record signals over a period of day or weeks, and in few instances, for several months. An electrode is needed, however, that can transmit signals accurately over a longer period, since repeated operations on a human to repair or replace an electrode are certainly undesirable. Freedom of movement is also often restricted by the bulky electrode structures used by present techniques. It would be advantageous to have a small structure that would not limit movement. A permanent electrode, along with a recording system which does not restrict movement would allow the gathering of data which, eventually, could enable paralyzed persons to interface with prosthetic devices in a way approaching normal motor functions, that is, with accuracy and precision.

SUMMARY OF THE INVENTION

Accordingly, the present invention provides an apparatus for long term recording of electrical signals transmitted by the brain. In a preferred embodiment the apparatus is an implantable neural electrode which, when placed in the brain or other area, can remain functional without causing significant trauma to the body or other deleterious effects. The electrode comprises an insulated conductive wire which at one end is adhered to a matable pin that can connect to a recording apparatus. The other end of the wire is connected to an insulating structure such as a hollow glass cone, which electrically insulates the wire from the rest of the brain. The wire is cemented within the cone with the terminus exposed. A segment of nerve, such as the sciatic nerve, is dissected from the body and placed inside the glass cone in contact with the exposed wire. When the electrode is implanted in the brain the neurites will grow into the glass cone and the nerve segment will serve as an anchor for the in-growing neurites. The contact between the nerve fibers and the exposed wire form an electrical circuit and the signal produced can be recorded by an extracorporeal recording device.

A method is provided for implanting the electrode whereby an incision is made in the scalp and a hole bored through the skull. The cone is placed in the grey matter and the pin is cemented to the bone with a biocompatible glue such as dental acrylic. A second electrode can be glued in proximity to the first electrode as an indifferent electrode. This second electrode can serve as ground and the differential voltage across the gap between the two electrodes measured, thereby providing a sensitive and accurate measurement of neural activity in the brain area where the cone is implanted.

It is therefore a principal object of the present invention to provide a means for long term recording of neural signals from the body.

It is another object of the present invention to provide an implantable neural electrode for transmitting and receiving signals to and from the body.

It is yet another object of the present invention to provide a means for transmitting an extracorporeal signal to the brain in order to control or stimulate motor activity.

It is another object of the present invention to provide a method for implanting a neural electrode that will transmit signals over an extended period of time, while not interfering with normal body functions.

DETAILED DESCRIPTION OF THE INVENTION

Figure 1:
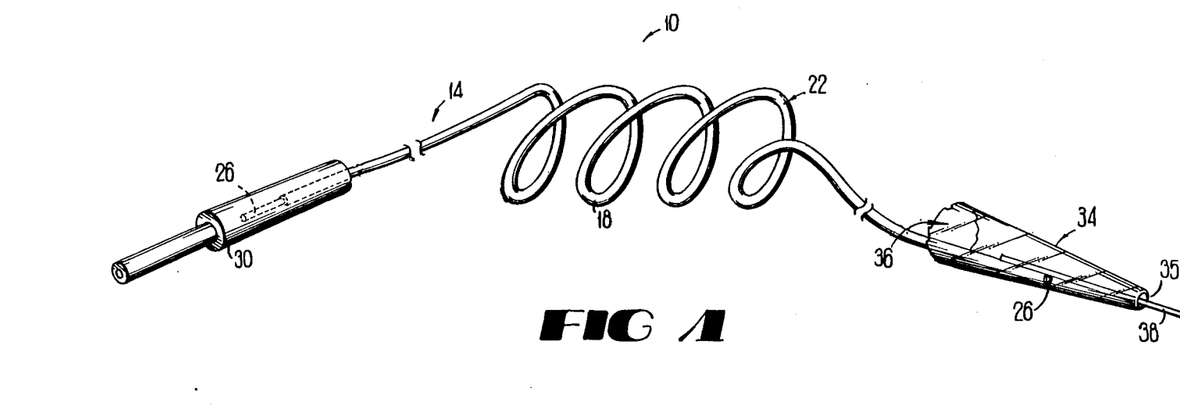
FIG. 1 is a prospective view of an implantable neural electrode.

The present invention provides an implantable neural electrode suitable for long term transmission of signals. Referring to the drawing in which like numerals describe like parts throughout the several figures, FIG. 1 is a prospective view of an implantable neural electrode in which electrode 10 is designed for implantation of a part of its structure within the body. Wire 14 can be made of fiber optic cable or any conductive material such as but not limited to metal, essentially metallic, and the like. Wire 14 is a conductive material insulated for substantially over its entire length to prevent electrical contact with the body other than in selected areas. It can be insulated by any of several common insulating materials known in the art. Wire 14 can be of any convenient diameter, preferably 1–1000 microns, more preferably 25 to 75 microns. In a preferred embodiment wire 14 is made of 0.003" diameter gold covered by Teflon® (a registered trademark of E.I. duPont de Nemours & Co. for polytetrafluoroethylene) insulation. Along part of its length wire 14 is coiled into at least one and preferably a plurality of resilient coils 22 to permit flexion of the wire without breaking or distorting. The coils reduce the likelihood of damage to the tissue when wire and the electrode are in place by allowing strain relief for small movements of the brain relative to the skull. The coils can be formed in any convenient manner; for example, a portion of wire 14 an be wrapped around a small diameter cylinder such a pin and the pin then removed from the formed coil. The coils are preferably formed on a part of wire 14 that will not be implanted beneath the skull or so deeply that the flexion is obviated.

An elongated metallic or other conducting material pin 30 contacts wire 14 in a manner allowing a conductive path to be established. Essentially, an end portion of wire 14 is stripped of insulation and the bare portion is soldered or otherwise joined to the inside of pin 30. The pin is capable of matably connecting with an extracorporeal complementary pin 31 that is connected to a recording device. Reference to a recording device 33 should be understood to include signal transmission and reception devices where the signal information is, at some point, transferred by radiowaves or fiber optics.

Insulator 34 is a hollow structure with an internal cavity having at least one and preferably two openings to allow for circulation of extracellular fluids. At least one of the openings is sufficiently large to admit wire 14. Insulator 34 can be of any regular or irregular shape. In the preferred embodiment, insulator 34 is a hollow cone-shaped structure so as to facilitate insertion into the body. Insulator 34 is composed of a biologically inert insulative substance such as but not limited to ceramic, plastic, polymeric cellulose, and the like. Insulator 34 is preferably made of glass which does not provoke a tissue reaction in the central nervous system.

In a preferred embodiment a thin-walled hollow glass tube such as a pipette is heated and drawn into a fine tube or cone. A portion of the tube is then broken off and used as insulator 34. As such, insulator 34 permits only a few neutons to come in proximity to wire 14 in an organized manner, rather than random contact, so as to produce a useful signal. The neurons that grow into insulator 34 should have similar movement-related properties. To accomplish this, end 26 of wire 14 distal to the pin is stripped of its insulation and exposed at the tip. This end is partially inserted into either opening of cone 34 and permanently affixed into place on the interior wall of cone 34, with the tip exposed, using any suitable adhesive, such as but not limited to methyl or butyl cyanoacrylate, parylene, or the like. This construction allows the recording of signals transmitted only by the nerve fibers in the immediate vicinity of exposed end 26, and excludes transmission of spurious signals from surrounding nerve tissue outside of insulator 34.

The signal is transmitted to the wire in at least one of several ways. Direct contact between the wire and the nerve fiber, which gives a stronger, more reliable signal, is preferable. Alternatively, body fluid, which has electroconductive properties, may bridge the gap between the wire and nearby nerve fiber. To enhance the signal contact the present invention incorporates a segment of nerve fiber 38 into the interior hollow area of insulator 34. A segment of nerve fiber 38 is dissected from a remote part of the body, such as the sciatic nerve or the like. Nerve segment 38 is then placed inside insulator 34 preferably in contact with exposed end 26 of wire 14. Nerve segment 38 can rest wholly within insulator 34 or extend outside of either one or both ends. Preferably, nerve segment 38 extends o outside of hole 35. Nerve segment 38 serves as an anchor to which nerve fibers in the cortex or other point of implantation can attach and grow. This provides a novel means for providing a long term stable electrode, within a nerve area, which can receive or transmit electrical signals.

Alternatively, it is possible to implant insulator 34 with wire 14 in the cortex without the use of a dissected nerve fiber as an anchor, and add a nerve growth stimulator to induce growth of the neurons within insulator 34 so as to come in proximity to or in contact with exposed end 26. Nerve growth can be stimulated by the use of any appropriate material, such as but not limited to, nerve growth factor, gangliosides, heart conditioned medium,neurite-inducing factor, epidermal growth factor, or the like.

Electrode 10 is implanted in a part of the body which gives access to neural activity and corresponds to the area of interest for measurement. For example, to analyze motor control, the electrode is implanted in the cortical motor, pre-motor or supplementary motor areas, or in the cerebellum. For recording visual signals, implantation would be in the visual cortex. The electrode could also be implanted in the spinal cord to monitor the neural activity of paraplegic subjects. In a preferred embodiment, the electrode is implanted in the grey matter of the cerebral cortex (preferably in the fifth level), giving access to the neurons that give origin to the corticospinal tract. In a preferred embodiment, implantation is performed no sooner than about 24 hours after fabrication of electrode 10 to allow time for any impurities associated with the glue or insulation to disperse.

Figure 2:
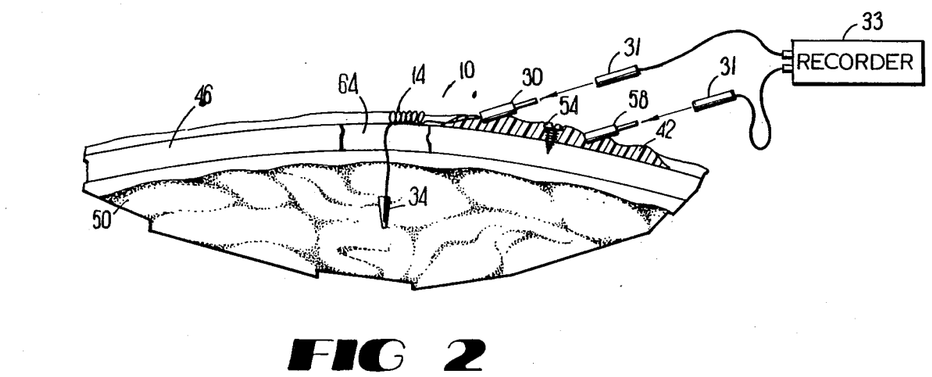
FIG. 2 is a cutaway view of a neural electrode implanted in the brain.

The method of the present invention can be illustrated by considering the implantation of an electrode in the brain of a rat as illustrated in FIG. 2. For implantation in the rat, anesthesia is provided by an intraperitoneal injection of 65 mg per kg of body weight of pentobarbital sodium (Nembutal$^{TM}$, Abbot Laboratories, N. Chicago, IL) after induction with halothane. To maintain anesthesia as the effect of pentobarbital diminishes, small doses of ketamine are given intramuscularly as required (10 to 20 mg per kg of body weight). Full sterile procedures are used throughout. The rat's head is held in a stereotaxis frame for stability during surgical manipulations.

The sciatic nerve or its branches in the posterior leg are exposed by an incision posterior to the knee. A scalp flap is opened with the incision on the left of midline. A 4 mm opening 64 is made on the left, posterior to bregma and, if necessary, extended a few millimeters with rongeurs to find an area of cortex that is relatively free of blood vessels. Next, a stainless steel bone screw 54 is inserted into a drilled hole and a small drop of dental acrylic cement is placed on bone that has been carefully scraped free of any periosteum (which results in better adhesion between the cement and the bone). The electrode is aligned and the dura opened. A length of sciatic nerve or one of its branches is now removed through the previously made leg incision and transferred to sterile saline. The nerve is trimmed and placed on a fine filament, such as a wire, hair, silk suture, or the like. In one embodiment, a length of hair (sterilized in alcohol) is cut from the rat's whiskers. The nerve segment 38 is allowed to partially dry out so that it sticks to the hair which is then inserted into insulator 34. The hair is then very gently pulled through insulator 34. A drop of saline is then placed on the hair an d cone 34. This results in reconstitution of the nerve to its previous size and allows the hair to be removed. Excess nerve is trimmed off. In some implantations the nerve will lie within the full length of insulator 34 and protrude out both ends. Though it might be easier to construct insulator 34 with a wide tip and a closed proximal end, it is preferable to have two openings for ease of circulation of extracellular fluids. Furthermore, instead of using the hair, a silk suture can be tied to one end of the nerve, threaded and pulled through insulator 34 so that the nerve comes to lie in insulator 34. The silk can then be removed by cutting the nerve.

The wire near insulator 34 can be bent to about a 70 degree angle, but there is wide latitude in what angle can be used. The electrode pin 30 is lowered until it lies on hardened adhesive 42, such as dental acrylic cement, and the tip of insulator 34 is carefully inserted into the cortex after opening the pia and making a shallow 1 mm cortical incision. Pin 30 is further cemented down except at its proximal end. An absorbent material, such as gelfoam pieces (Upjohn Co.) can then be laid all around wire 14 and the cortex to act as a "bed" for electrode 10. Further gelfoam can be laid on top of wire 14 and all around electrode 10, and the fascia is closed (such as with 6/0 silk) followed by skin closure of the scalp and leg. The closure gently maintains pressure on cone 34 within the brain.

The signals produced by the nerve fibers in proximity to or touching nerve segment 38 or the bare end 26 of wire 14 will be electrically conducted through the wire to pin 30, which communicates with a recording device 33 outside of the body. In one embodiment of the present invention signals are received from the body in order to analyze neural functions of the body. In an alternative embodiment, electrical signals are transmitted from an extracorporeal transmitter to the nerve fibers in proximity to the electrode. The effects of this stimulation can be observed as motor or other activity.

In an alternative embodiment bipolar recording can be used to improve signal quality. Monopolar recording, which uses one electrode, while sufficient for some purposes, can be improved using a reference electrode. Signals received from electrode 10 can include spurious and background "noise" derived from such sources as other body electricity, static electricity, AM or FM reception, fluorescent light fixtures, machines, and the like, which can reduce sensitivity of the measurements. By using a second electrode which does not receive neural signals, the differential between the two electrodes can be determined as a more accurate measurement of neural activity. In this embodiment, the primary electrode 10 is the same as discussed above. A secondary electrode 58 is mounted by cement is proximity to pin 30 on the skull in a manner similar to the mounting of pin 30. Reference electrode 58 can be similar to pin 30. The two are positioned 5–10 mm from each other. The recording instrument is set up to measure the signals coming from both electrodes. The extraneous signals received by the primary electrode will be substantially the same as those received by the reference electrode, with the added signal of the nerve fiber. The difference between the two signal effectively cancels out the extraneous signals yielding a net signal composed essentially of the neural signal.

Figures 3, 4, 5:
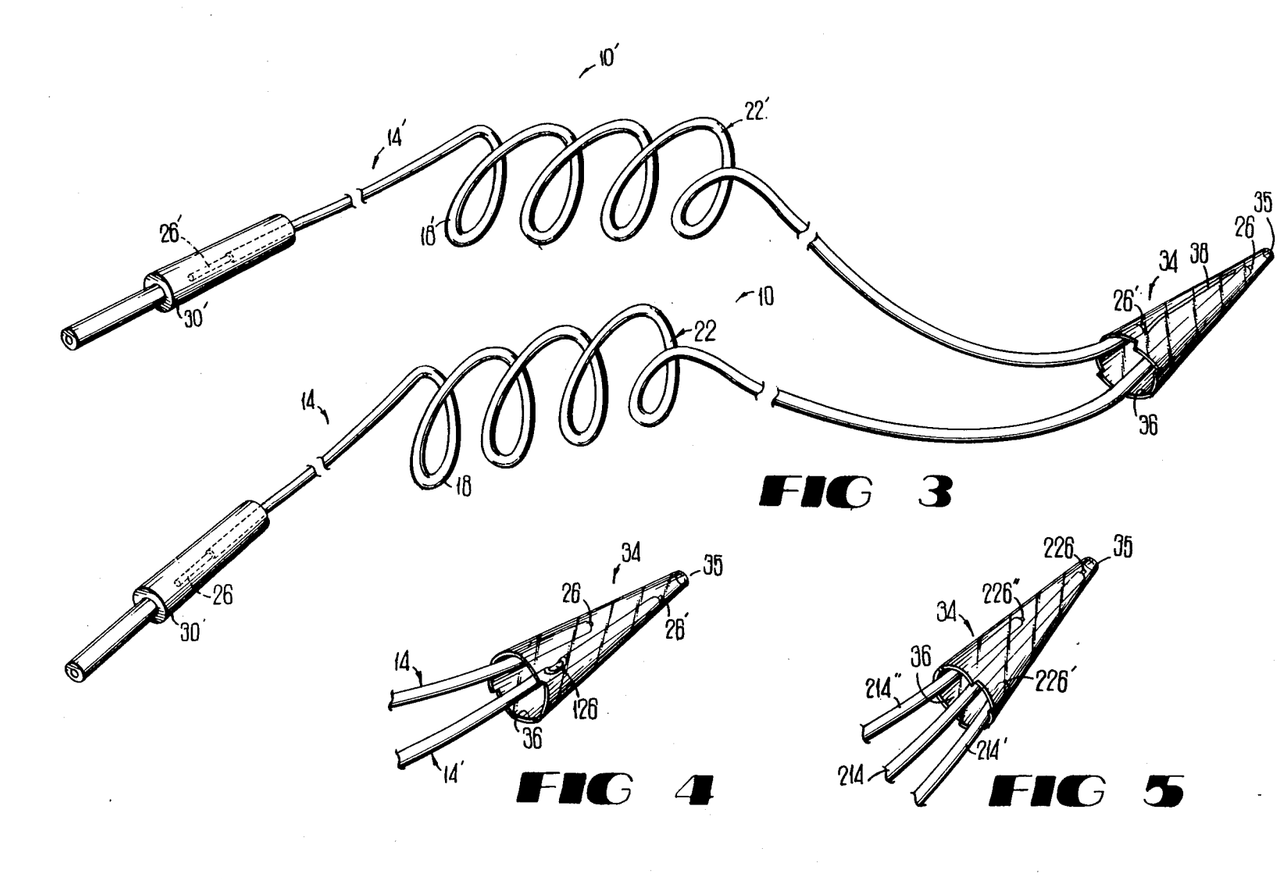
FIG. 3 is a perspective view of an alternative embodiment of an implantable neural electrode having two discrete wires.
FIG. 4 is a perspective view of an alternative embodiment where there are three exposed portions of two wires.
FIG. 5 is a perspective view of an alternative embodiment where three discrete wires are used.

FIG. 3 illustrate a perspective view of an alternative embodiment of an implantable neural electrode having two discrete wires. In this alternative embodiment two wires, 14 and 14', are affixed to the inner surface of insulator 34. Wire 14 is positioned with exposed end 26 at the distal opening 35 of insulator 34 and wire 14' is positioned with exposed end 26' at proximal opening 36. Wire 14' is composed of material similar to wire 14 and contains essentially the same coil structure and insulation. Also, wire 14' is connected to a pin 30' in substantially the same manner as for the connection of wire 14 to pin 30. Nerve segment 38 (not shown in FIG. 3) can be positioned so as to be in proximity to or contacting either one, or both, or neither of exposed ends 26 and 26'. The electrical activity across the electrical gap created between the two exposed wires 26 and 26' is measured as an indication of neural electrical activity within insulator 34. The advantage is that by recording the difference in electrical potentials between the two wires, only the tissue between the wires can contribute to the change in electrical potential. This prevents neural signals arising outside insulator 34 from interfering with the signals arising within the insulator.

FIG. 4 is a perspective view of an alternative embodiment wherein there are three exposed portions of two wires. In still another alternative embodiment, two wires 14 and 14' are affixed within insulator 34 as described above. In this embodiment however, wire 14 has exposed end 26 located in a central portion of the interior cavity of insulator 34 (see FIG. 4). Wire 14' has one exposed end 26' located in proximity to distal opening 35 and a second predetermined exposed portion 126 located in proximity to proximal opening 36. The addition of a third exposed of a third exposed portion 126 reduces the possibility of longitudinal currents from the outside electrode effecting the recording accuracy.

FIG. 5 is a perspective view of an alternative embodiment where three discrete wires are used in which two wires are grounds and a third is active. In accordance with this aspect, wire 214 is positioned with exposed end 226 in proximity to distal opening 35. Wire 214' is positioned with exposed end 226' in proximity to proximal opening 36. Wire 214" is positioned with exposed end 226" located between exposed ends 226 and 226' in the interior of insulator 34. Wire 214" is the active recording wire while wires 214 and 214' are grounded wires. This configuration can also increase sensitivity by decreasing spurious signal interferences from outside insulator 34.

Figure 6:
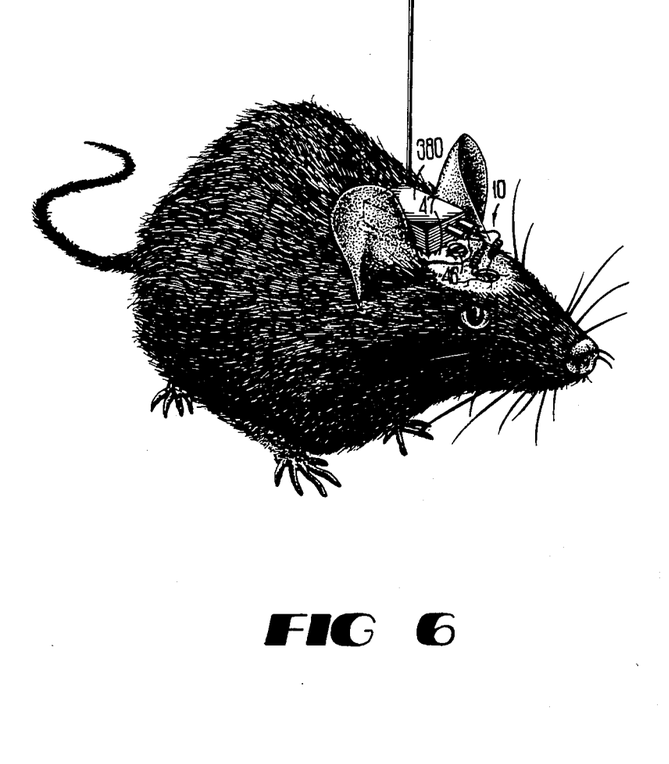
FIG. 6 is a perspective view of an electrode implanted in a rat and connected to a transmitter/receiver device attached to the skull of the rat.

FIG. 6 is a perspective view of an electrode implanted in a rat and connected to a transmitter/receive device attached to the skull of the rat. In an alternative embodiment, a frequency modulated ("FM") transmitter can be attached to the electrode so that the signals can be transmitted without having wires traversing the skin. This aspect of the present invention is shown in FIG. 6, in which transmitter 380 is mounted on skull bone 46 by cement 47, and connected via pin 30 to electrode 10 implanted in the brain. The electrode and bone hole 46 are shown exposed for purposes of illustration. In practice, this area will be covered by the skin of the rat. This would avoid any possible source of entry of pathogenic organisms. The FM transmitter can be cemented to the skull. The union is strengthened by a screw 54 that is inserted into the skull. The screw also provides strain relief. The cement can flow around the screw and transmitter before hardening. The transmitter is a very high frequency ("VHF") FM unit employing a modulated subcarrier. This approach permits adequate range and frequency response as well as freedom from artifacts. Battery drain can be minimized (and thus useful life extended) by using low power transistors and low-drain circuitry. In addition, life can be further extended by using a switching arrangement such as a magnetic reed switch, which applied powers only when needed.

Surface mount technology ("SMT") can be used in the construction of the transmitter to achieve small size, reliability, and economy. This technology was developed for high-volume production. Relatively conventional construction procedures, using soldering and small printed circuit boards, can also be employed, resulting economical small-scale fabrication.

Since the transmitter will be implanted in a living animal, special encapsulation procedures are required, both to ensure biocompatibility, and to prevent the infusion of body fluids into the circuitry, which could cause a malfunction. A suitable encapsulating material is used. The transmitter is then coated with tissue-compatible silastic or other suitable material and then sterilized. The permeable silastic will allow sterilization o f the entire unit, while protecting the sealant against mechanical abrasion which could expose an unsterilized subsurface.

In an alternative embodiment, component 380 is a FM receiver which can be used to provide signals to the brain so that the results of an applied signal can be studied and/or controlled.

In still another alternative embodiment, component 380 is an FM transceiver so that signal can both be transmitted to and received from the brain.

Figures 7, 8:
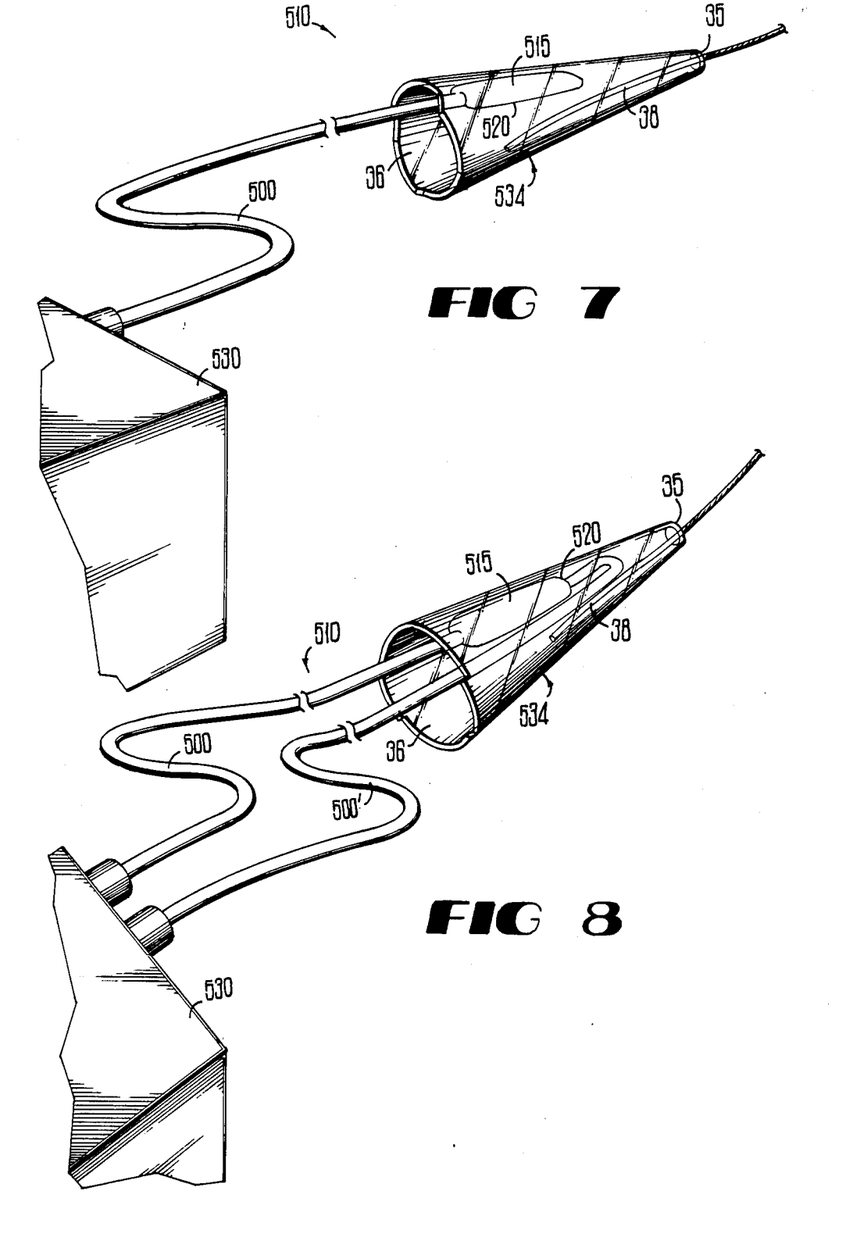
FIG. 7 is a perspective view of an alternative embodiment wherein fiber optic cable is used to carry a signal to the recording device.
FIG. 8 is a perspective view of an alternative embodiment wherein fiber optic cable used to carry a signal to the recording device contains two fiber optic cables.

In another embodiment of the present invention, fiber optic cable can be used in place of metallic wire. FIG. 7 is a perspective view of an electrode 510 illustrating a light opaque insulator 534 having openings 35 and 36. A nerve segment 38 is disposed at least partially within the cavity. Fiber optic cable 500 is connected partially within the cavity through an opening 35 or 36 in the cavity. Associated with the inner wall of the insulator 534 is a discrete dye chamber 515 containing an appropriate dye and contained by translucent membrane 520. Fiber optic cable 500 is connected to extend signal recording/transmitting device 530. Cable 500 can be co-axial, multi-axial or side-by-side cables such that there are at least two light paths: one transmits a light beam from device 530 and another receives light after being modified by the dye.

Insulator 534 is optically opaque so as to prevent spurious signals from outside insulator 34 entering the dye chamber and is composed of the material described herein above. Dye chamber 515 is a discrete container attached to the inner wall of insulator 534 containing an electrochemically active dye. The dye is retained in the chamber by membrane 520, which is electron optically translucent. Fiber optic cable 500 is composed of light communicating material known in the art.

Nerve fiber 38 is activated, or "fixed" in response to motor or other activity. When this occurs the surface potential of the nerve reverses polarity via a sodium ion, with a resulting emission of electrons. By being in proximity to the nerve fiber 38, the dye in chamber 515 receives the emitted electrons, which cause an electrochemical change in the optical properties of the dye. The light beam striking the dye chamber 515 is changed by the dye, and the modulated light is transmitted back to device 530, which records the change. The light characteristics which can be changed include intensity, frequency, wavelength and the like. The amount of change is correlative with the degree of electrical activity of nerve fiber 38.

FIG. 8 shows an alternative embodiment similar to the one just described wherein a pair of fiber optic cables are used on opposite sides of dry chamber 515. See FIG. 8. One cable transmits light from device 530 to the dye chamber 515 and the other receives light passing through the chamber and returns the light to device 530. The characteristics of the light will be altered by the presence of the dye. As the dye's properties are altered by the nerve fiber activity, the light pulse or beam is also modified, resulting in a detectable change. Thus the recording device 530 can register indirectly the amount of electrical activity of neurites in the insulator 534 spatially associated with the dye. Outside electrical chemical effects are minimized by the opaque insulator 534.

The present invention can be used as a communication tool for handicapped people to reach the outside world. Many handicapped persons can generate nerve signals from the brain but cannot activate the muscles, for any of a number of reasons, including paralysis, birth defects, nerve severance or damage, cerebral palsy, amyotrophic lateral sclerosis ("Lou Gehrig's" Disease) severely limited motor coordination, or the like. Implanting an electrode as in the present invention can enable such persons to transmit nerve signals to the electrode which in turn can be amplified and connected to a control device which manipulates other devices. In this way, the electrode 10 can replaced damaged or missing nerve connections in the body. The electrode of the present invention can also be used to study nerve damage.

It should be understood that the foregoing relates only to a preferred embodiment of the present invention and that numerous modifications or alterations may be made without departing from the spirit and scope of the invention as set forth as set forth in the appended claims.

What is claimed is:

1. A neural electrode capable of being implanted in operative relation with neural structure in a body, comprising:
    a flexible electrical conductor, insulated except for a predetermined area, for conducting an electrical signal between a predetermined location within said body and predetermined point outside said body;
    a biologically inert electrically insulative structure defining an interior cavity and having at least one opening into the cavity, said insulative structure surrounding at least said predetermined area of said conductor and electrically substantially isolating said conductor from points other than said predetermined within said body; and
    a nerve segment separate from the neural structure, said nerve segment being disposed in electroconductive relation with the predetermined area and being at least partially within the insulative structure so as to facilitate the growth, within said insulative structure, of neurites associated with the neural structure,
    whereby the electrical conductor is capable of receiving electrical signals from the body or transmitting electrical signals to the body.

2. The electrode of claim 1, wherein said electrical conductor comprises a flexible implantable wire.

3. The electrode of claim 2, wherein said wire is formed into a serires of coils along a predetermined portion of its length for permitting flexion of said wire in response to movement.

4. The electrode 2, wherein said insulative structure comprises a hollow cone having a least one opening, and said electrical conductor extends into said opening.

5. The electrode of claim 1, wherein said insulative structure is a hollow tubular element having at least one opening, and said electrical conductor extends into said opening.

6. The electrode of claim 1, wherein said electrical conductor is secured to an inner wall of said insulative structure.

7. A method for receiving or transmitting electrical signals relative to neural structure of a body, comprising:
    (a) implanting an electrode within said body, said electrode prepared by the steps comprising:
        (i) preparing a conducting means insulated except for a predetermined area and operative for conducting an electrical signal between a predetermined location within said body and a predetermined point outside said body;
        (ii) surrounding at least said predetermined are of said conducting means with an insulating means for electrically isolating said conducting means from points other than said predetermined location within said body; and
        (iii) placing a nerve segment separate from the neural structure in electroconductive relation with the predetermined area and at least partially within the insulating means, so as to facilitate the growth of neurites within the insulating means: and
    (b) receiving electrical signals from said body or transmitting electrical signals to said body by way of said electrode and said nerve segment,w which bridges said conducting means to at least one of said neurites.

8. The method of claim 7, comprising the further step of adhering said electrode to said body.

9. The method of claim 7, comprising the further step of adhering said electrode is said body by adhering a predetermined portion of said conducting means to bone matter of the body by means of a biocompatible cement 10. The method of claim 9, wherein said cement is secured to said bone, in addition to adhesion, by a fastening means secured to said bone.

11. The method of claim 9, comprising the further steps of mounting a screw in said bone and extending partially out of said bone, and fastening said cement to said bone by the screw in addition to adhesion.

12. The method of claim 7, comprising the further steps of placing said nerve segment on said conducting means and allowing the nerve segment to dry thereon, so that the nerve segment thereby adheres to said conducting means.

13. The method of claim 7, wherein at least one of said neurites grows so as to contact said nerve segment, thereby producing a bioelectrical contact between said neurite and said electrode.

14. The method of claim 7, wherein said nerve segment is removed from said body before being placed in said electroconductive relation with the predetermined are of said conducting.

15. The method of claim 14, wherein said nerve segment comprises a portion of a sciatic nerve.

16. The method as in claim 7, comprising the further step of dissecting the nerve segment from a remote part of said body, prior to placing the nerve segment in electroconductive relation with the conducting means.

17. A method for receiving or transmitting electrical signals from or to a body, comprising:
  (a) making an incision in said body;
  (b) placing an electrode in proximity to viable neurons, said electrode prepared by the steps comprising:
    (i) preparing a conducting means insulated except for a predetermined area for conducting an electrical signal between a predetermined location within said body and a predetermined point outside said body;
    (ii) surrounding at least said predetermined are of said conducting means with an insulating means for electrically isolating said conducting means from points other than said predetermined location within said body; and
    (iii) placing a nerve segment separate from the body in electroconductive relation with the predetermined location and at least partially within the insulating means, so as to facilitate the growth of neurites within the insulating means; and
  (c) securing said electrode in a biocompatible manner so as to favor the growing of neurites within said electrode;
  (d) closing said incision so that a portion of said electrode extends extracorporeally; and
  (e) using said extracorporeally extending portion of the electrode for receiving said electrical signals produced by said body or transmitting said electrical signals to said body.

18. The method of claim 17, comprising the step of selecting said conducting means from the group consisting of a metallic and an essentially metallic material.

19. The method of claim 18, wherein said conducting means comprises gold wire.

20. A neural electrode capable of being implanted in a body, comprising:
  (a) signal generating means for generating signals in response to nerve fiber activity proximate thereto;
  (b) an insulative structure having at least one opening and an interior cavity having a nerve fiber segment separate from the body disposed therein in proximity to said signal generating means;
  (c) an electrical wire connected to said signal generating means for conducting said signals between said signal generating means within said body and a predetermined point outside said body; and
  (d) a portion of said signal generating means is in proximity to said nerve fiber segment within said insulative structure, so as to facilitate the growth of neurites within the insulative structure.

21. The neural electrode of claim 20, further comprising a signal recording and generating means in communication with said electrical wire.

* * * * *